United States Patent
Chamberlain et al.

(10) Patent No.: US 10,557,736 B2
(45) Date of Patent: Feb. 11, 2020

(54) PREDICTIVE DIAGNOSTICS SYSTEMS AND METHODS USING VACUUM PRESSURE CONTROL VALVES

(71) Applicant: MKS Instruments, Inc., Andover, MA (US)

(72) Inventors: David Brian Chamberlain, Hooksett, NH (US); Vladislav Davidkovich, Reading, MA (US); Scott Benedict, Nashua, NH (US); Gordon Hill, Arlington, MA (US)

(73) Assignee: MKS Instruments, Inc., Andover, MA (US)

( * ) Notice: Subject to any disclaimer, the term of this patent is extended or adjusted under 35 U.S.C. 154(b) by 295 days.

(21) Appl. No.: 15/581,875

(22) Filed: Apr. 28, 2017

(65) Prior Publication Data

US 2017/0328756 A1 Nov. 16, 2017

Related U.S. Application Data

(60) Provisional application No. 62/333,989, filed on May 10, 2016.

(51) Int. Cl.
*G01F 9/00* (2006.01)
*G01N 17/00* (2006.01)

(52) U.S. Cl.
CPC ............ *G01F 9/001* (2013.01); *G01N 17/008* (2013.01)

(58) Field of Classification Search
CPC ....................................................... G01F 9/001
(Continued)

(56) References Cited

U.S. PATENT DOCUMENTS 4,322,972 A * 4/1982 Karjala .................. F04B 23/02
137/546
6,302,130 B1 10/2001 Ohmi et al.
(Continued)

FOREIGN PATENT DOCUMENTS

JP 2011069407 4/2011
JP 2015190496 11/2015

OTHER PUBLICATIONS

International Search Report and Written Opinion from corresponding PCT Application No. PCT/US2017/031498, International Filing Date May 8, 2017, dated Jul. 25, 2017.

*Primary Examiner* — Walter L Lindsay, Jr.
*Assistant Examiner* — Philipmarcus T Fadul
(74) *Attorney, Agent, or Firm* — Burns & Levinson, LLP; Joseph M. Maraia; Steven M. Mills

(57) ABSTRACT

Calibration of a valve in a vacuum system and providing a diagnostic indication in the vacuum system using the calibration includes measuring conductance of the valve as a function of angular valve position and generating a conductance calibration map or function for use during operation of the valve. An actual angular valve position is set based on the received set point angular valve position and a difference between the measured valve conductance and a predefined metric of conductance versus angular valve position. An actual system conductance and a difference between the actual system conductance and a reference system conductance for the system are determined. The diagnostic indication of a fault in the system is generated based on the actual angular valve position of the valve and the difference between the actual system conductance and the reference system conductance for the system.

16 Claims, 7 Drawing Sheets

(58) Field of Classification Search
USPC .......................................................... 73/168
See application file for complete search history.

(56) References Cited

U.S. PATENT DOCUMENTS

| | | | |
|---|---|---|---|
| 2009/0078038 A1* | 3/2009 | Ushigusa | G01F 1/42 |
| | | | 73/195 |
| 2013/0306172 A1 | 11/2013 | Volovec | |
| 2014/0183394 A1 | 7/2014 | Yamada et al. | |
| 2015/0057816 A1* | 2/2015 | Schick | G05D 7/0635 |
| | | | 700/282 |

* cited by examiner

| A | B | C | D | E |
|---|---|---|---|---|
| Actual Shaft Position (% OPEN) | Example Golden Curve Conductance: Sg | Example DUT Curve Conductance: Sd | POSd->Sg | Sd->POSg |
| 0 | 0.02 | 0.02 | 0.00 | 0.00 |
| 1 | 1.02 | 0.03 | 10.00 | 0.01 |
| 2 | 2.02 | 0.06 | 14.14 | 0.04 |
| 3 | 3.02 | 0.11 | 17.32 | 0.09 |
| 4 | 4.02 | 0.18 | 20.00 | 0.16 |
| 5 | 5.02 | 0.27 | 22.36 | 0.25 |
| 6 | 6.02 | 0.38 | 24.49 | 0.36 |
| 7 | 7.02 | 0.51 | 26.46 | 0.49 |
| 8 | 8.02 | 0.66 | 28.28 | 0.64 |
| 9 | 9.02 | 0.83 | 30.00 | 0.81 |
| 10 | 10.02 | 1.02 | 31.62 | 1.00 |
| 11 | 11.02 | 1.23 | 33.17 | 1.21 |
| 12 | 12.02 | 1.46 | 34.64 | 1.44 |
| 13 | 13.02 | 1.71 | 36.06 | 1.69 |
| 14 | 14.02 | 1.98 | 37.42 | 1.96 |
| 15 | 15.02 | 2.27 | 38.73 | 2.25 |
| 16 | 16.02 | 2.58 | 40.00 | 2.56 |
| 17 | 17.02 | 2.91 | 41.23 | 2.89 |
| 18 | 18.02 | 3.26 | 42.43 | 3.24 |
| 19 | 19.02 | 3.63 | 43.59 | 3.61 |
| 20 | 20.02 | 4.02 | 44.72 | 4.00 |
| 21 | 21.02 | 4.43 | 45.83 | 4.41 |
| 22 | 22.02 | 4.86 | 46.90 | 4.84 |
| 23 | 23.02 | 5.31 | 47.96 | 5.29 |
| 24 | 24.02 | 5.78 | 48.99 | 5.76 |
| 25 | 25.02 | 6.27 | 50.00 | 6.25 |
| 26 | 26.02 | 6.78 | 50.99 | 6.76 |
| 27 | 27.02 | 7.31 | 51.96 | 7.29 |
| 28 | 28.02 | 7.86 | 52.92 | 7.84 |
| 29 | 29.02 | 8.43 | 53.85 | 8.41 |
| 30 | 30.02 | 9.02 | 54.77 | 9.00 |
| 31 | 31.02 | 9.63 | 55.68 | 9.61 |
| 32 | 32.02 | 10.26 | 56.57 | 10.24 |
| 33 | 33.02 | 10.91 | 57.45 | 10.89 |
| 34 | 34.02 | 11.58 | 58.31 | 11.56 |
| 35 | 35.02 | 12.27 | 59.16 | 12.25 |
| ... | ... | ... | ... | ... |
| 95 | 95.02 | 90.27 | 97.47 | 90.25 |
| 96 | 96.02 | 92.18 | 97.98 | 92.16 |
| 97 | 97.32 | 94.11 | 98.49 | 94.09 |
| 98 | 98.02 | 96.06 | 98.99 | 96.04 |
| 99 | 99.02 | 98.03 | 99.50 | 98.01 |
| 100 | 100.02 | 100.02 | 100.00 | 100.00 |

Fig. 5

PREDICTIVE DIAGNOSTICS SYSTEMS AND METHODS USING VACUUM PRESSURE CONTROL VALVES

RELATED APPLICATION

This application is related to and claims priority to U.S. Provisional Patent Application No. 62/333,989, filed on May 10, 2016, the entire contents of which are incorporated herein by reference.

BACKGROUND

1. Technical Field

The present disclosure is related to vacuum pressure control valves, and, in particular, to systems and methods using predictive diagnostics in connection with vacuum pressure control valves.

2. Discussion of Related Art

A typical vacuum-based processing system, such as, for example, a semiconductor processing system, often includes one or more valves and a vacuum pump positioned downstream of a processing chamber to control the flow of fluids through the chamber. These fluids flowing through the chamber can include, for example, reactive gases used to etch or coat a semiconductor wafer in the chamber. The vacuum pump creates a pressure difference between a location upstream of the valve and a location downstream of the valve. Flow through the chamber is controlled by varying the conductance of the valve by changing the degree to which the valve is open/closed.

Butterfly valves are commonly used in vacuum pressure control systems, such as those employed in semiconductor fabrication systems. A butterfly valve, or "flapper valve," typically includes a thin flapper coaxially disposed within a passageway through the valve housing. The flapper is secured to the valve assembly by a rotatable valve shaft extending laterally across the passageway. Rotation of the valve shaft controls the position of the flapper with respect to the valve housing. The conductance of a butterfly valve is controlled by varying the position of the flapper between open (100% open) and closed (0% open) positions.

In such processing systems, various factors can cause degradation in system performance over time. For example, in deposition tools, deposition by-products can build up in the valve and/or in the pumping line. This build-up can change the fluid conductance of one or more components of the vacuum system. Also, a flexible seal between the flapper and the valve body can wear over time, which can also alter the conductance performance of the vacuum system, and, in particular, the valve.

SUMMARY

According to a first aspect, a method for calibrating a valve in a vacuum system is provided. According to the method, conductance of the valve as a function of angular valve position is measured. A conductance map or function for the valve is determined by comparing the measured valve conductance to a predefined metric of conductance versus angular valve position. The conductance calibration map or function is stored for use during operation of the valve.

A difference between the measured valve conductance and the predefined metric of conductance versus angular valve position can be used in determining the conductance map or function. During operation, a set point angular valve position based on a desired conductance of the valve can be received. Actual angular valve position of the valve can be set based on the received set point angular valve position and the difference between the measured valve conductance and the predefined metric of conductance versus angular valve position. An actual system conductance and a difference between the actual system conductance and a reference system conductance for the system can be determined. A diagnostic indication of a fault in the system can be generated based on the actual angular valve position of the valve and the difference between the actual system conductance and the reference system conductance for the system. If the actual angular valve position is relatively low and the actual system conductance is greater than the reference system conductance, in a low-conductance valve, the diagnostic indication can be that a flapper seal of the low-conductance valve is worn. If the actual angular valve position is relatively low and the actual system conductance is less than the reference system conductance, in a non-sealing valve, the diagnostic indication can be that deposition by-products have accumulated on at least one of a valve wall and a flapper of the valve. The relatively low angular valve position can be below 20 degrees. If the actual angular valve position is relatively high and the actual system conductance is less than the reference system conductance, in a low-conductance valve, the diagnostic indication can be at least one of an at least partial blockage in a conduit of the system and degradation of a pump in the system. If the actual angular valve position is relatively high and the actual system conductance is less than the reference system conductance, in a non-sealing valve, the diagnostic indication can be at least one of an at least partial blockage in a conduit of the system and degradation of a pump in the system. The relatively high angular valve position can be greater than 50 degrees.

According to another aspect, a method for providing a diagnostic indication in a vacuum system using a valve is provided. According to the method, a set point angular valve position based on a desired conductance of the valve is received. An actual angular valve position of the valve is set based on the received set point angular valve position and a difference between the measured valve conductance and a predefined metric of conductance versus angular valve position. An actual system conductance and a difference between the actual system conductance and a reference system conductance for the system are determined. A diagnostic indication of a fault in the system is generated based on the actual angular valve position of the valve and the difference between the actual system conductance and the reference system conductance for the system.

If the actual angular valve position is relatively low and the actual system conductance is greater than the reference system conductance, in a low-conductance valve, the diagnostic indication can be that a flapper seal of the low-conductance valve is worn. If the actual angular valve position is relatively low and the actual system conductance is less than the reference system conductance, in a non-sealing valve, the diagnostic indication can be that deposition by-products have accumulated on at least one of a valve wall and a flapper of the valve. The relatively low angular valve position can be below 20 degrees. If the actual angular valve position is relatively high and the actual system conductance is less than the reference system conductance, in a low-conductance valve, the diagnostic indication can be at least one of an at least partial blockage in a conduit of the system and degradation of a pump in the system. If the actual angular valve position is relatively high and the actual system conductance is less than the reference system conductance, in a non-sealing valve, the diagnostic indication can be at least one of an at least partial blockage in a conduit of the system and degradation of a pump in the system. The relatively high angular valve position can be greater than 50 degrees.

BRIEF DESCRIPTION OF THE DRAWINGS

The present disclosure is further described in the detailed description which follows, in reference to the noted plurality of drawings by way of non-limiting examples of embodiments of the present disclosure, in which like reference numerals represent similar parts throughout the several views of the drawings.

FIG. 5 includes a table corresponding to the graph of FIG. 4.

DETAILED DESCRIPTION OF PREFERRED EMBODIMENTS

Embodiments described herein provide for valve-to-valve repeatability of conductance versus commanded valve, e.g., flapper, position, regardless whether the commanded position is externally or internally sourced, e.g., during closed-loop pressure control. The embodiments support chamber matching and copy-exact requirements, because each valve provides the same performance as a function of the command provided to the valve.

According to some exemplary embodiments, a method for calibrating a valve includes measuring conductance of the valve as a function of valve position and determining a conductance calibration map or function for the valve by comparing the measured valve conductance to a predefined metric of conductance versus valve position. The method also includes storing the conductance map or function for use during operation of the valve.

Fluid conductance is a measure of how effectively a fluid moves through a structure or substance. In a vacuum system, the conductance (C) of a fluid through a pipe or conduit is determined by the relationship:

$$C = \frac{Q}{(P_1 - P_2)}; \quad (1)$$

where Q is the total mass flow of the fluid through the conduit, $P_1$ is the pressure upstream, and $P_2$ is the pressure downstream.

Conductance of a valve is typically controlled by changing the valve opening between open and closed positions. Valve performance is typically reported by manufacturers based on nominal, minimum, and maximum expected performance. However, actual conductance of a valve can vary widely between different valves. Many properties of a valve, other than the degree to which it is open or closed, affect the actual conductance performance. For example, mechanical tolerances of components and variation in assembly of the components can contribute significantly to the variation in conductance of one valve relative to another. While parts may be selected based on precise measurement specifications and assembly can be customized to achieve exacting tolerances, it is impractical to do so in a production environment.

Figure 1:
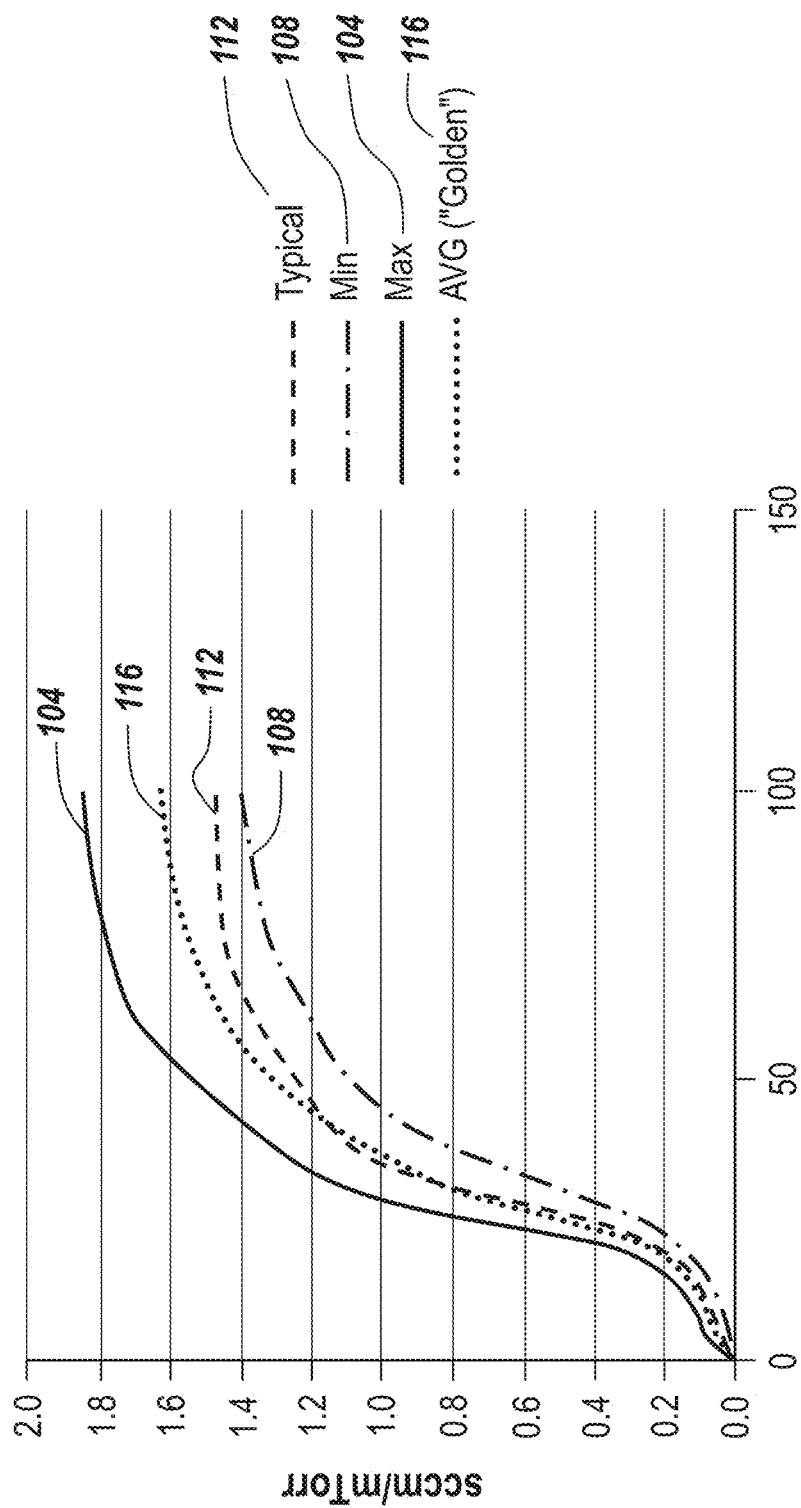
FIG. 1 includes a graph of conductance versus valve position for several similar valves.

FIG. 1 is a plot of conductance versus valve position for several similar valves. The Y-Axis is in units of standard cubic centimeters per milliTorr, corresponding to a pressure difference between an upstream location and downstream location relative to the valve. The X-Axis is in units of percent openness of the valve, varying between 0% open, i.e., closed, and 100% open. Curve 104 is the maximum expected conductance of a typical valve, and curve 108 is the minimum expected conductance of the valve. Curve 116 is the conductance for an exemplary valve in a batch of produced valves, and curve 112 depicts typical conductance performance for valves in the batch.

Semiconductor manufacturers often have multiple processing systems, i.e., tools, which perform the same function. They expect each of the systems to operate in the same manner with minimal calibration or setup, particularly at initial tool installation and commissioning. For example, the manufacturers expect to be able to control the conductance of a valve using the same process recipes without having to calibrate each valve during installation or a service interval. Furthermore, manufacturers expect that each valve provide the same conductance for a specified, commanded or reported position. By way of example, the possible variation in conductance between a maximum conductance (curve 104) and minimum conductance (curve 108) is larger than desired for many applications. In general, it is desirable for each valve to operate with the same conductance, e.g., conductance curve 116, as a function of the commanded or reported position of the valve, i.e., % open in this instance. Embodiments described herein provide methods by which each valve provides a known conductance in response to a commanded position.

Figure 2:
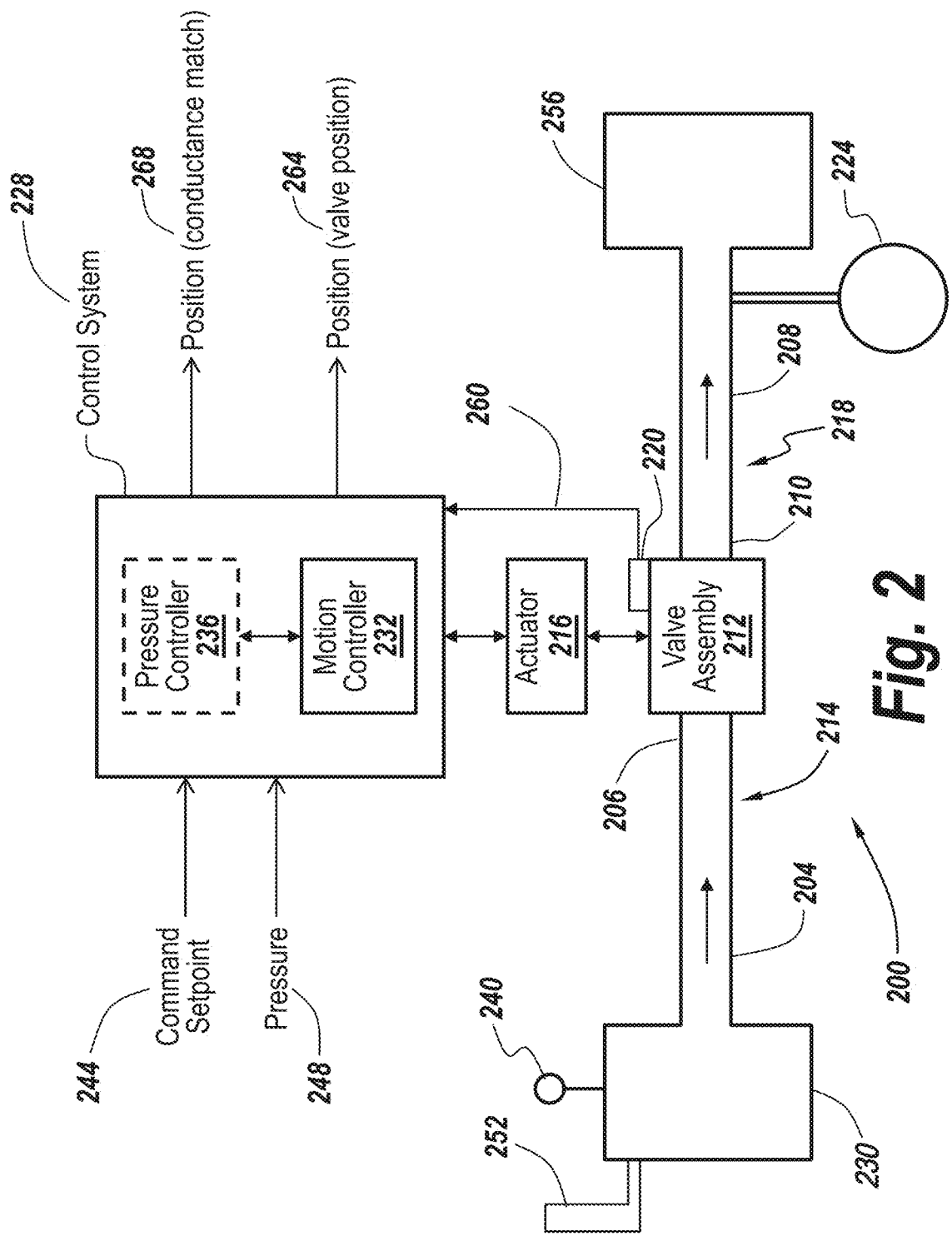
FIG. 2 includes a schematic block diagram of a processing system, according to an exemplary embodiment.

FIG. 2 includes a schematic block diagram of a processing system 200, according to an exemplary embodiment. The processing system 200 includes a process chamber 230 including a conduit 204 coupled to an output of process chamber 230. System 200 also includes a valve assembly 212 coupled to an outlet 206 of conduit 204. Valve assembly 212 is also coupled to an inlet 210 of a second conduit 208. System 200 also includes a pump 224 coupled to second conduit 208. Pump 224 draws fluid from conduit 208 to create a pressure difference between a location upstream 214 of valve assembly 212 and a location downstream 218 of valve assembly 212.

System 200 also includes an actuator 216 operatively connected to valve assembly 212. Actuator 216 controls the operation of valve assembly 212 to vary, for example, the flow of fluid through valve assembly 212 from conduit 204 to conduit 208. In some embodiments, valve assembly 212 includes a butterfly valve, and actuator 216 changes the position of a flapper in valve assembly 212 relative to the passageway through valve assembly 212. In this manner, actuator 216 affects the conductance of valve assembly 212 by altering the degree to which the valve is open/closed. System 200 may also include a valve position sensor 220, e.g., an optical or mechanical encoder, which measures the position of the flapper as it changes during operation.

Figure 3A:
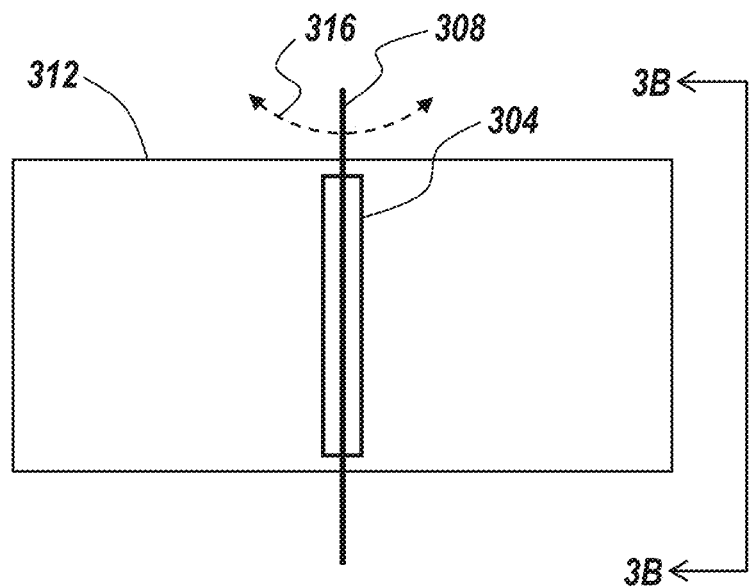
FIG. 3A includes a schematic diagram of a valve assembly, according to an exemplary embodiment.
Figure 3B:
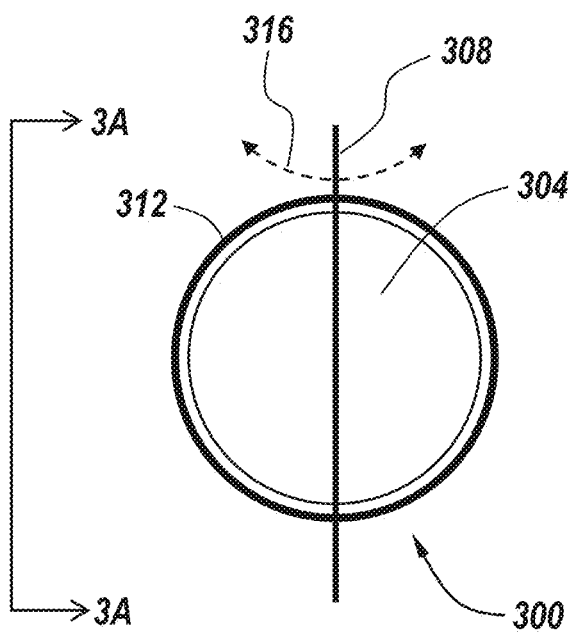
FIG. 3B includes a schematic side view of the valve assembly of FIG. 3A, according to an exemplary embodiment.

FIGS. 3A and 3B are schematic illustrations of a valve assembly 300 according to an illustrative embodiment. The valve assembly 300 is a flapper valve assembly and includes a flapper 304. The flapper 304 is secured to the valve assembly 300 by a rotatable valve shaft 308 that extends laterally across a passageway 312 of the valve assembly 300. Rotation of the valve shaft 308 is shown by dashed arrow 316. Rotation of the valve shaft 308 by an actuator, e.g., actuator 216 of FIG. 2, controls the position of flapper 304 with respect to passageway 312 of valve assembly 300. The conductance of valve assembly 300 is controlled by varying the position of flapper 304 between open and closed positions (shown as 100% closed in FIG. 3B).

Referring to FIG. 2, system 200 also includes a control system 228 operatively connected to actuator 216. Control system 228 provides signals to actuator 216 and receives various input signals. Control system 228 controls the operation of actuator 216 to control valve assembly 212. Control system 228 includes a motion controller 232 and, optionally, a pressure controller 236. In one embodiment, motion controller 232 receives various signals and information and outputs various signals and information, and outputs motion control signals to actuator 216. Optional pressure controller 236 is used in some embodiments with motion controller 232 to calculate control signals to be provided to actuator 216 to control the pressure in process chamber 230 by varying the position of the flapper in valve assembly 212. The pressure can be measured using, for example, a pressure transducer 240 coupled to process chamber 230.

In some implementations, a valve assembly, e.g., valve assembly 212, is used to control the conductance of a gas exiting processing chamber 230. The gas travels along conduit 204 and through valve assembly 212. The gas then travels through conduit 208 to a reclaim system 256 for safe disposal. A command set point 244 (position set point in this embodiment) is provided to control system 228. Position set point 244 is the desired position of the flapper in valve assembly 212 relative to the passageway passing through valve assembly 212. Position s 244 is typically predetermined for a specific set of processing steps for which processing chamber 230 is intended so that a specific flow conductance is achieved. In some embodiments, position set point 244 is a 0-10 volt DC analog signal proportional to the desired flapper valve position; with 0 volts corresponding to fully closed and 10 volts corresponding to fully open. Alternative signals are used in alternative embodiments. For example, in some embodiments, the signal is a digital signal with values proportional to the desired flapper position, or a digital signal that the control system uses to increment or decrement the position of the flapper relative to the passageway.

In operation, gas is provided to process chamber 230 via gas inlet 252, and motion controller 232 of control system 228 receives position set point 244 and compares it to the actual position of the flapper in valve assembly 212. A signal 260 corresponding to the actual position of the flapper is provided to control system 228 by valve position sensor 220, although in some embodiments the actual position may be derived from previous (open loop) position commands provided by the motion controller to the actuator. Motion controller 232 calculates the error between position set point 244 and actual position signal 260. Motion controller 232 then outputs a command signal to actuator 216 to change the flapper position until the error is zero (or below a desired threshold). Motion controller 232 outputs a signal that has the characteristics desired for the movement of the flapper, e.g., flapper position, speed, overshoot, etc.

Valve assembly 212 may not provide the desired valve conductance after achieving the position corresponding to the desired position set point 244 because of variations in the manufacturing of each valve assembly. This may also be due to system usage and wear factors, such as accumulation of deposition by-products on various components of system 200, such as chamber 230, pump 224, conduits/lines 204, 208, valve body and/or flapper; worn flapper seals; blockage in conduits/lines 204, 208; and/or degradation of pump 224. The variations in the valve assembly result in variations in the conductance of valve assembly 212. Therefore, it is desirable for control system 228 to modify position set point 244 so that the signals provided to actuator 216 by control system 228 account for the variation in the conductance of valve assembly 212.

Figure 4:
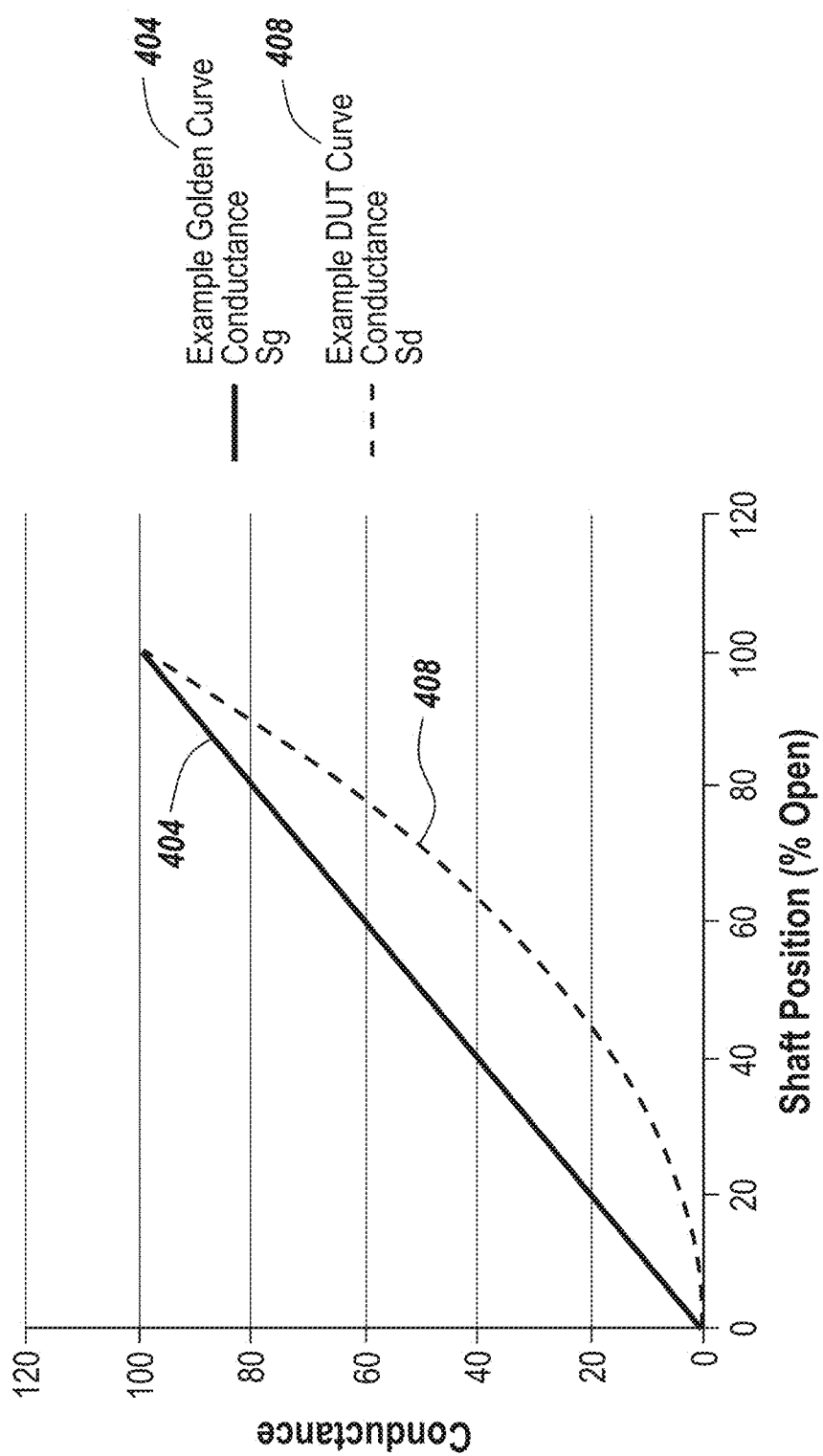
FIG. 4 includes a graph of conductance versus shaft position for a flapper valve assembly, according to an exemplary embodiment.

FIG. 4 includes a graph of conductance versus shaft position for a flapper valve assembly, according to an exemplary embodiment. The Y-axis is conductance and the X-axis is the shaft position for positions ranging from 0% (fully closed) to 100% (fully open). Curve 404 is the desired conductance of the valves as a function of shaft position. Each valve does not provide this specific conductance performance because of the variations described herein. Curve 408 is the conductance of a specific valve which does not match the desired conductance shown by curve 404.

FIG. 5 is a table 500 corresponding to the plot of FIG. 4. Column A of table 500 is the shaft position (only a portion of the values are provided for clarity of illustration purposes). Values are provided from 0% open (completely closed) to 35% open and 95% open to 100% open (completely open). Column B of the table 500 is the conductance for the desired performance of the valves (corresponding to curve 404 of FIG. 4), also referred to as the "golden unit." Column C of the table 500 is the conductance for the performance of the specific valve (corresponding to curve 408 of FIG. 4).

By way of example, if the specific valve was commanded to a shaft position of 10% open (arrow 504) it would provide a conductance of 1.02 (column C, arrow 512), not the desired conductance of 10.02 (column B, arrow 508). Therefore, in order for valve assembly 212 to provide the desired conductance of 10.02, control system 228 must output a different signal to actuator 216 so that the valve position is commanded to be at a different valve position than the 10%. Therefore, actuator 216 must move the valve position of the specific valve to approximately 31.62 (arrow 516) to achieve a conductance of 10.02 for the specific valve. The values in column D of table 500 (conductance calibration factors) are the positions at which actuator 216 must place valve assembly 212 so valve assembly 212 provides the desired conductance of curve 404 of FIG. 4. In some embodiments, the values in column D are stored in a look-up table in control system 228, and control system 228 outputs a signal to actuator 216 to achieve that valve position in valve assembly 212 in response to position set point 244 provided by a user.

In this embodiment, control system 228 outputs various signals, including actual valve position 264 (the same as position signal 260) and a conductance match position signal 268. In some exemplary embodiments, conductance match position signal 268 is equal to conductance set point 244. Hence, the approach of the present disclosure satisfies end-user need to have a known and repeatable position output variable versus the actual conductance a valve is producing. In the case in which the valve is providing closed-loop pressure control, the end-user is typically monitoring the reported position from the valve to enable controls, such as, for example, well-known SPC controls, associated with valves manufactured and sold by SPC Company of Torrance, Calif., USA. In contrast, traditional valves typically only report the actual shaft position of the valve's flapper. The conductance match position signal 268 of the exemplary embodiments is generated by sensing the actual shaft position, which is known from the motion control system being run. From the internal calibration data described herein, the actual conductance being provided by the valve is determined. The valve references the stored reference table of a "golden" valve's conductance versus position and reports the conductance match position in conductance match position signal 268 as the position at which the "golden" valve would have produced the conductance the valve is providing at that instant in time.

According to exemplary embodiments, when the valve is used as a position controller, conductance match signal 268 relates to a conductance match position equal to conductance set point 244. When the valve is used as a pressure controller, conductance match position is not equal to conductance set point 244, since conductance set point 244 in this case is a pressure set point command. Instead, in this case, conductance match position signal 268 is generated according to the approach described above in detail.

The values in column D could, alternatively, be stored in memory, e.g., in a look-up table, in actuator 216 or valve assembly 212 and be configured to correct the operation of the valve in response to command set point 244. In some embodiments, an equation is generated that approximates the values in column D as a function of commanded set point 244 values so no look-up table is required. Rather, control system 228 determines what signal to provide to actuator 216 based on the equation which is a function of command set point value 244. The equation may be generated by, for example, interpolation or curve fit techniques.

Column E of table 500 of FIG. 5 is the position the golden unit would be at to produce the same conductance as the specific valve for a given shaft position. If optional pressure controller 236 is active and the shaft position of valve assembly 212 is modified during closed-loop control, column E is used to output the equivalent position at which the "golden" valve would generate the actual conductance being delivered by the valve.

As noted above, in processing systems such as those described above in detail, various factors can cause degradation in system performance over time. For example, in deposition tools, deposition by-products can build up in the valve and/or in the pumping line, i.e., plumbing/conduits. This build-up can result in reduced pumping line diameter and/or pump performance and can change the fluid conductance of one or more components of the vacuum system; it can also result in reduced pumping speed. In response to this degradation, in a non-sealing valve, the valve can compensate by setting to a larger valve opening position. Also, in a non-sealing valve, this deposition build-up can reduce a gap between the flapper and the walls of the valve bore or flow passage, thus reducing the valve conductance, in some cases, to values near zero conductance. In this case, the valve can compensate by closing less, i.e., by setting to a smaller valve angle. In the case of a sealing valve, where a flexible seal is provided at the outer edge of the flapper between the flapper and the walls of the valve body bore or passage can wear over time, which can also alter the conductance performance of the vacuum system. In this case, the deposition build-up and/or valve seal wear can prevent the valve from reaching zero conductance at normal valve angle settings. In this case, the valve can compensate by closing more, i.e., by setting a smaller valve angle. Therefore, in accordance with the present disclosure, in all of these cases, the valve position can be correlated to a degree of degradation in one or more components of the system.

According to some exemplary embodiments, conductance match position signal 268 is used as a position reporting technique which allows end users to use throttle valve position as a predictive diagnostic variable for chamber matching and fault detection and classification of other faulty components. This approach satisfies commonly expressed end-user need to have a known and repeatable position output variable, as opposed to the actual conductance a valve is producing.

Another useful output is "% Conductance." This variable would be the $N_2$ equivalent conductance (l/s) produced by the valve at each position under a specific set of test conditions. The variable % Conductance is a normalized output relative to a standard gas, e.g., $N_2$, under specified conditions. As an example, for a given valve size, the 100% open conductance for $N_2$ may be 100 l/s. At 80% open, it may be 90 l/s, and so forth. In this illustrative example, when the valve is 100% open physically and providing 100 l/s conductance, the "% Conductance" output would be 100%. When the valve is 80% open physically and providing 90 l/s, the "% Conductance" output would be 90%. The reason it is expressed as "% Conductance" and not just "Conductance" is that end users can use the valve with many different gases and gas mixes, and the measured conductance is a function of gas type. Thus, generating an output as an absolute unit (l/s) is avoided in favor of the normalized "% Conductance." This characterization provides the user with a transferable repeatable standard by which to validate that the valve is providing known calibrated performance. This conductance may be of interest as a primary variable, but there will still be a valve-to-valve variability in conductance versus position. On the other hand, conductance versus conductance match position will have very tight valve-to-valve repeatability.

The more typical position reporting variables of "step counts based position" and "encoder based position" are available from the valve. This allows end users to monitor for second-order dependencies (if they exist) of actual shaft position versus conductance. However, the primary benefit of first-order valve-to-valve repeatability for reported position versus conductance will be satisfied via conductance match position described above.

The pressure dynamics in the downstream pressure control systems can be described as:

$$V_{chamber} \frac{dP_{chamber}}{dt} = Q_{inlet} - S_{system} \cdot (P_{chamber} - P_{pump}); \quad (2)$$

where:
$V_{chamber}$—chamber volume
$P_{chamber}$: pressure inside the chamber
$P_{pump}$: pressure at pump input
$Q_{inlet}$: inlet gas flow
$S_{system}$: combined system conductance.

Under normal circumstances, the pressure at the pump is substantially lower than the controlled pressure inside the chamber and thus can be ignored.

The combined system conductance $S_{system}$ can be described as a series connection of individual conductances of the elements comprising the downstream pressure control system: chamber, valve, foreline (conduit), and pump:

$$S_{system} = \frac{1}{\frac{1}{C_{chamber}} + \frac{1}{C_{foreline}} + \frac{1}{C_{valve}} + \frac{1}{C_{pump}}}, \quad (3)$$

where:
$C_{chamber}$—chamber conductance
$C_{foreline}$: foreline conductance
$C_{pump}$: conductance (pumping speed) of pump
$C_{valve}$: throttle valve conductance.

The valve conductance $C_{valve}$ is a highly nonlinear function of valve angle θ, variable between 0% open and 100% open: $C_{valve}=f(\theta)$.

For a typical downstream pressure control application, the following relationships between various system components will hold true:

Case I: θ≤10% open, i.e., relatively small valve angle. In this case, system conductance is dominated by the valve conductance only, that is:
$C_{valve} \ll C_{chamber}$
$C_{valve} \ll C_{foreline}$
$C_{valve} \ll C_{pump}$ In this case, equation (3) can be re-written as an approximation:
$S_{system} \approx C_{valve}$ Considering this relationship, system diagnostics can be performed based on the knowledge of valve angle and system conductance $S_{system}$, which is a generally available variable. As a result, in this case of small valve angle, any substantial variation of $S_{system}$ can be attributed to a change in valve conductance. Specifically, for a low-conductance throttle valve (such as F-seal, Q-seal, etc.), the damage or wear of the sealing element will result in higher system conductance, as illustrated in FIG. 6, and can be used for in-situ diagnostics of valve health.

Figure 6:
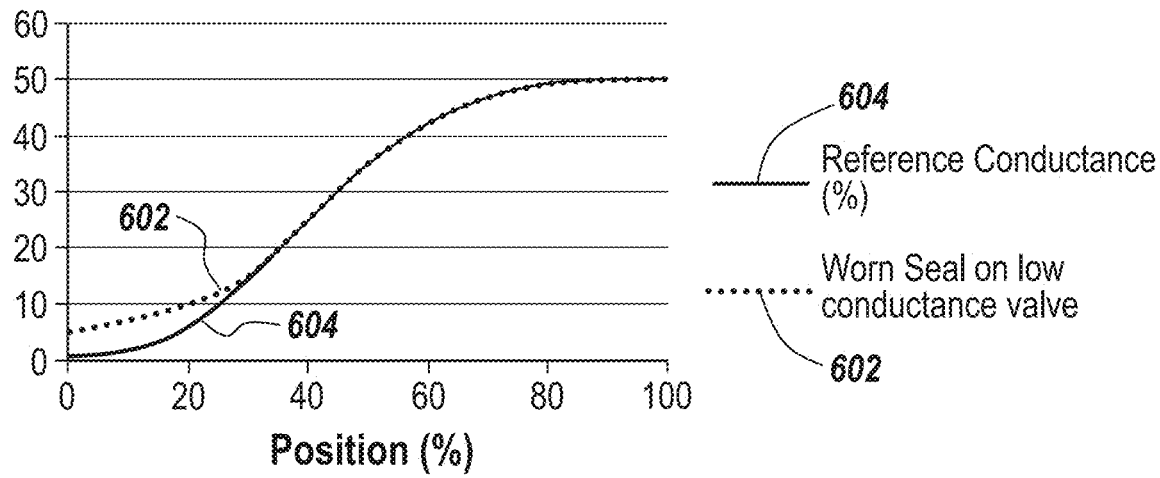
FIG. 6 includes a graph of conductance versus flapper position in an exemplary low-conductance flapper valve, illustrating the case of a worn flapper seal.

FIG. 6 includes a graph of conductance versus flapper position in an exemplary low-conductance flapper valve, illustrating the case of a worn flapper seal. FIG. 6 illustrates variation of system conductance due to wear of flapper seal. FIG. 6 includes an actual system conductance $S_{system}$ curve 602 and a reference conductance curve 604. As illustrated in FIG. 6, in the case of a worn flapper seal, the system conductance $S_{system}$ will be detected to be higher than the expected reference conductance at small valve opening angles.

Figure 7:
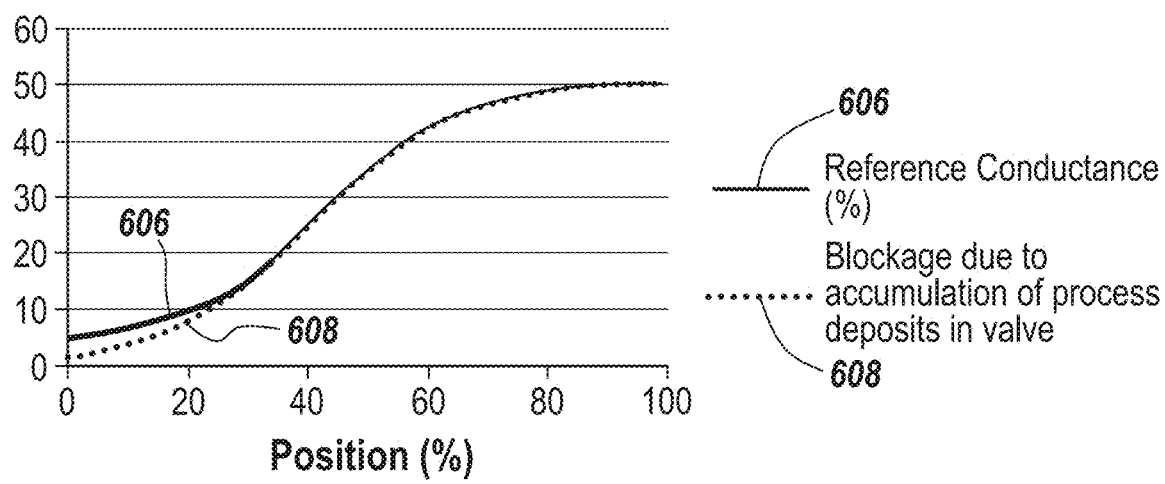
FIG. 7 includes a graph of conductance versus flapper position in an exemplary non-sealing flapper valve, illustrating the case of accumulation of deposits on the valve body wall or flapper.

For non-sealing valves, the contamination of valve body due to chemical deposits during its operation can be detected as a decrease of system conductance $S_{system}$ compared to the reference values at low openings, as illustrated in FIG. 7. FIG. 7 includes a graph of conductance versus flapper position in an exemplary non-sealing flapper valve, illustrating the case of accumulation of deposits on the valve body wall or flapper. FIG. 7 illustrates variation of system conductance due to contamination of non-sealing valve flapper and body. FIG. 7 includes an actual system conductance $S_{system}$ curve 608 and a reference conductance curve 606. As illustrated in FIG. 7, in the case of accumulation of deposits on the valve body wall or flapper in a non-sealing valve, the system conductance $S_{system}$ will be detected to be lower than the expected reference conductance at small valve opening angles.

Case II: θ≥60% open, i.e., relatively large valve opening. In this case, foreline, i.e., plumbing (conduit/pipe), conductance and pump conductance are much smaller than the valve conductance and the chamber conductance. System conductance is dominated by the foreline (plumbing, conduit/pipe) conductance and pump conductance. In this case, equation (3) can be written as the approximation:

$$S_{system} \approx \frac{1}{\frac{1}{C_{plumbing}} + \frac{1}{C_{pump}}}$$

The effect of the seal is negligible at large valve openings. For both low-conductance and non-sealing butterfly valves, the reduction in the measured system conductance can be attributed to the degradation of pump performance or to blockage in plumbing, i.e., conduit/pipe, as illustrated in FIGS. 8 and 9.

Figure 8:
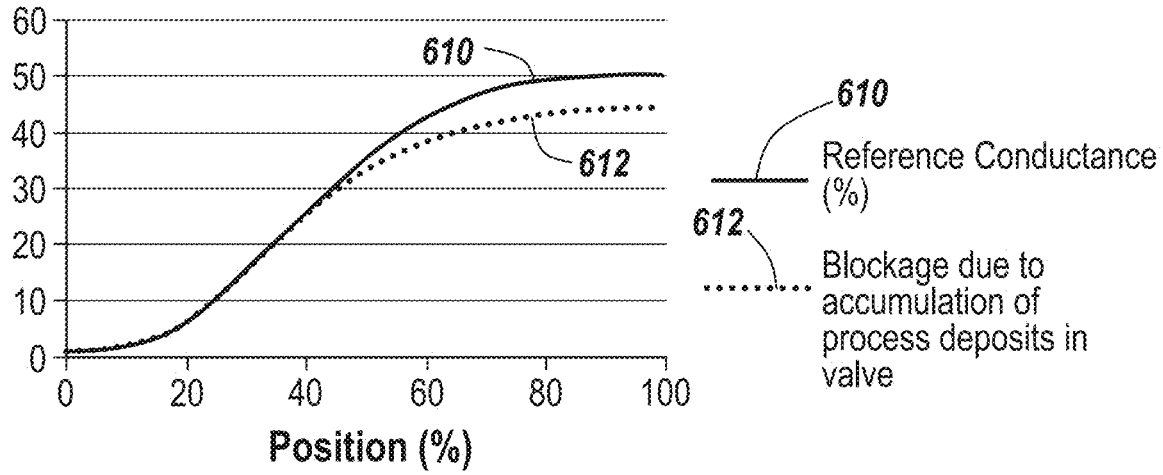
FIG. 8 includes a graph of conductance versus flapper position in an exemplary low-conductance flapper valve, illustrating the case of blockage in a pumping line or pump degradation.

FIG. 8 includes a graph of conductance versus flapper position in an exemplary low-conductance flapper valve, illustrating the case of blockage in a plumbing line, i.e., conduit/pipe or pump degradation. FIG. 8 illustrates change in system conductance due to line blockage or pump degradation in a low-conductance valve. FIG. 8 includes an actual system conductance $S_{system}$ curve 612 and a reference conductance curve 610. As illustrated in FIG. 8, in the case of line blockage or pump degradation in a low-conductance valve, the system conductance $S_{system}$ will be detected to be lower than the expected reference conductance at relatively large valve opening angles.

Figure 9:
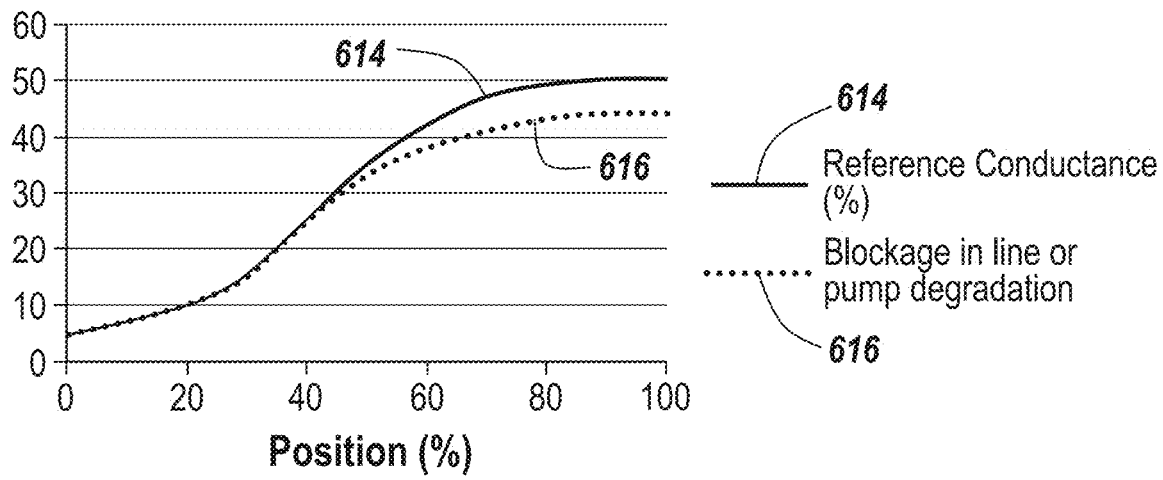
FIG. 9 includes a graph of conductance versus flapper position in an exemplary non-sealing flapper valve, illustrating the case of blockage in a pumping line or pump degradation.

FIG. 9 includes a graph of conductance versus flapper position in an exemplary non-sealing flapper valve, illustrating the case of blockage in a pumping line or pump degradation. FIG. 9 illustrates change in system conductance due to line blockage or pump degradation in a non-sealing valve. FIG. 9 includes an actual system conductance $S_{system}$ curve 616 and a reference conductance curve 614. As illustrated in FIG. 9, in the case of line blockage or pump degradation in a non-sealing valve, the system conductance $S_{system}$ will be detected to be lower than the expected reference conductance at relatively large valve opening angles.

Thus, in general, these diagnostics allow an end user, by observing which part of the conductance curve is changing, to conclude faults such as valve contamination, flapper seal wear, foreline blockage, and/or pump degradation.

In some exemplary embodiments, an implementation will utilize recipe timemark triggers that will be coordinated with the tool operation as follows:

Tool runs baseline process.

I/O with valve accepts an input that marks timemark triggers, i.e., RecordMark1, RecordMark2

At each mark, the valve records and stores in memory its position, recorded pressure, and internally estimated process parameters (gas flow)

During wafer production, the valve accepts a different trigger from the tool, that indicates that the recipe is passing through the same original mark points: i.e. ReadMark1, ReadMark2

At each mark point, the valve applies logic to determine if the conductance curve $S_{system}$ has shifted to the point where it passes some threshold. The valve will then issue a warning back to the tool with some indications as to the change, and likely causes of the change.

In this exemplary embodiment, the details of the communication format between the tool and the valve can be as shown in Table 1.

transducer placement will provide further differentiation between clogging the upstream plumbing versus downstream plumbing and pump degradation.

According to some exemplary embodiments, an alternative to the timemark approach is to perform a complete system learn routine during the idle time of the tool. This will generate the complete system conductance curve $S_{system}$ as plotted above. An advantage of this approach is that a more continuous curve compared to specific operating points obtained using the timemark approach.

In this application, including the definitions below, the term 'module' or the term 'controller' may be replaced with the term 'circuit.' The term 'module' may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or

TABLE 1

Proposed commands and interface to tool

| Command | Direction | Function |
| --- | --- | --- |
| Record Mark_n | Tool to Valve | Valve records pressure control conditions during "Process of Record" or reference conditions at a particular recipe step. |
| ReadMark n | Tool to Valve | Request for valve to output diagnostics at this point in recipe |
| Conductance Delta n | Valve to Tool (response to a Read Mark n) | quantitative output of deviation from actual conductance to that recorded during Process of Record |
| Average Conductance Delta (n) | Valve to Tool (response to a Read Mark n) | quantitative output of deviation from actual conductance to that recorded during Process of Record, but averaged over multiple (i) samples at recipe step n |
| Standard Deviation | Valve to Tool (response to a Read Mark n) | |
| Diagnostic Output | Valve to Tool (response to a Read Mark n) | One of several status:<br>a. Normal<br>b. System Conductance degrading (conductance at high valve position is reduced)<br>c. Flapper Gap reduced<br>d. Fseal worn/failed<br>e. Pump speed degrading<br>f. Buildup in valve reducing system conductance<br>g. Unknown |

According to some exemplary embodiments, another enhancement of the implementation includes the exchange of gas information between the tool and the valve. This allows for the use of a three-dimensional system conductance table with conductance being a nonlinear function of valve position and gas composition, that is, $S_{system}=f(\theta, \text{gas composition})$.

According to some exemplary embodiments, yet another enhancement of the diagnostic approach described herein in detail utilizes results from the use of both upstream and downstream pressure information, denoted as $P_{chamber}$ and $P_{pump}$ in equation (2) above. An effective placement of the upstream transducer is immediately at the valve inlet and of the downstream transducer is at the valve outlet. This group) that executes code; a memory circuit (shared, dedicated, or group) that stores code executed by the processor circuit; other suitable hardware components that provide the described functionality; or a combination of some or all of the above, such as in a system-on-chip.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

While the present inventive concept has been particularly shown and described with reference to exemplary embodiments thereof, it will be understood by those of ordinary skill in the art that various changes in form and details may be made therein without departing from the spirit and scope of the present inventive concept as defined by the following claims.

The invention claimed is:

1. A method for calibrating a valve in a vacuum system, comprising:
   measuring conductance of the valve as a function of angular valve position;
   determining a conductance map or function for the valve by comparing the measured valve conductance to a predefined metric of conductance versus angular valve position;
   storing the conductance calibration map or function for use during operation of the valve, wherein a difference between the measured valve conductance and the predefined metric of conductance versus angular valve position is used in determining the conductance map or function;
   during operation, receiving a set point angular valve position based on a desired conductance of the valve, and setting actual angular valve position of the valve based on the received set point angular valve position and the difference between the measured valve conductance and the predefined metric of conductance versus angular valve position;
   determining an actual system conductance and determining a difference between the actual system conductance and a reference system conductance for the system; and
   generating a diagnostic indication of a fault in the system, the diagnostic indication being based on the actual angular valve position of the valve and the difference between the actual system conductance and the reference system conductance for the system; wherein
   if the actual angular valve position is relatively low and the actual system conductance is greater than the reference system conductance, in a low-conductance valve, the diagnostic indication is that a flapper seal of the low-conductance valve is worn.

2. The method of claim 1, wherein the relatively low angular valve position is below 20 degrees.

3. A method for providing a diagnostic indication in a vacuum system using a valve, the method comprising:
   receiving a set point angular valve position based on a desired conductance of the valve;
   setting actual angular valve position of the valve based on the received set point angular valve position and a difference between the measured valve conductance and a predefined metric of conductance versus angular valve position;
   determining an actual system conductance;
   determining a difference between the actual system conductance and a reference system conductance for the system; and
   generating a diagnostic indication of a fault in the system, the diagnostic indication being based on the actual angular valve position of the valve and the difference between the actual system conductance and the reference system conductance for the system; wherein,
   if the actual angular valve position is relatively low and the actual system conductance is greater than the reference system conductance, in a low-conductance valve, the diagnostic indication is that a flapper seal of the low-conductance valve is worn.

4. The method of claim 3, wherein the relatively low angular valve position is below 20 degrees.

5. A method for calibrating a valve in a vacuum system, comprising:
   measuring conductance of the valve as a function of angular valve position;
   determining a conductance map or function for the valve by comparing the measured valve conductance to a predefined metric of conductance versus angular valve position; and
   storing the conductance calibration map or function for use during operation of the valve wherein a difference between the measured valve conductance and the predefined metric of conductance versus angular valve position is used in determining the conductance map or function;
   during operation, receiving a set point angular valve position based on a desired conductance of the valve; and setting actual angular valve position of the valve based on the received set point angular valve position and the difference between the measured valve conductance and the predefined metric of conductance versus angular valve position;
   determining an actual system conductance and determining a difference between the actual system conductance and a reference system conductance for the system; and
   generating a diagnostic indication of a fault in the system, the diagnostic indication being based on the actual angular valve position of the valve and the difference between the actual system conductance and the reference system conductance for the system; wherein
   if the actual angular valve position is relatively low and the actual system conductance is less than the reference system conductance, in a non-sealing valve, the diagnostic indication is that deposition by-products have accumulated on at least one of a valve wall and a flapper of the valve.

6. The method of claim 5, wherein the relatively low angular valve position is below 20 degrees.

7. A method for calibrating a valve in a vacuum system, comprising:
   measuring conductance of the valve as a function of angular valve position;
   determining a conductance map or function for the valve by comparing the measured valve conductance to a predefined metric of conductance versus angular valve position; and
   storing the conductance calibration map or function for use during operation of the valve wherein a difference between the measured valve conductance and the predefined metric of conductance versus angular valve position is used in determining the conductance map or function;
   during operation, receiving a set point angular valve position based on a desired conductance of the valve; and setting actual angular valve position of the valve based on the received set point angular valve position and the difference between the measured valve conductance and the predefined metric of conductance versus angular valve position;
   determining an actual system conductance and determining a difference between the actual system conductance and a reference system conductance for the system; and
   generating a diagnostic indication of a fault in the system, the diagnostic indication being based on the actual angular valve position of the valve and the difference between the actual system conductance and the reference system conductance for the system; wherein
   if the actual angular valve position is relatively high and the actual system conductance is less than the reference system conductance, in a low-conductance valve, the diagnostic indication is at least one of an at least partial blockage in a conduit of the system and degradation of a pump in the system.

8. The method of claim 7, wherein the relatively high angular valve position is greater than 50 degrees.

9. A method for calibrating a valve in a vacuum system, comprising:
   measuring conductance of the valve as a function of angular valve position;
   determining a conductance map or function for the valve by comparing the measured valve conductance to a predefined metric of conductance versus angular valve position; and
   storing the conductance calibration map or function for use during operation of the valve wherein a difference between the measured valve conductance and the predefined metric of conductance versus angular valve position is used in determining the conductance map or function;
   during operation, receiving a set point angular valve position based on a desired conductance of the valve; and setting actual angular valve position of the valve based on the received set point angular valve position and the difference between the measured valve conductance and the predefined metric of conductance versus angular valve position;
   determining an actual system conductance and determining a difference between the actual system conductance and a reference system conductance for the system; and
   generating a diagnostic indication of a fault in the system, the diagnostic indication being based on the actual angular valve position of the valve and the difference between the actual system conductance and the reference system conductance for the system; wherein,
   if the actual angular valve position is relatively high and the actual system conductance is less than the reference system conductance, in a non-sealing valve, the diagnostic indication is at least one of an at least partial blockage in a conduit of the system and degradation of a pump in the system.

10. The method of claim 9, wherein the relatively high angular valve position is greater than 50 degrees.

11. A method for providing a diagnostic indication in a vacuum system using a valve, the method comprising:
    receiving a set point angular valve position based on a desired conductance of the valve;
    setting actual angular valve position of the valve based on the received set point angular valve position and a difference between the measured valve conductance and a predefined metric of conductance versus angular valve position;
    determining an actual system conductance;
    determining a difference between the actual system conductance and a reference system conductance for the system; and
    generating a diagnostic indication of a fault in the system, the diagnostic indication being based on the actual angular valve position of the valve and the difference between the actual system conductance and the reference system conductance for the system; wherein,
    if the actual angular valve position is relatively low and the actual system conductance is less than the reference system conductance, in a non-sealing valve, the diagnostic indication is that deposition by-products have accumulated on at least one of a valve wall and a flapper of the valve.

12. The method of claim 11, wherein the relatively low angular valve position is below 20 degrees.

13. A method for providing a diagnostic indication in a vacuum system using a valve, the method comprising:
    receiving a set point angular valve position based on a desired conductance of the valve;
    setting actual angular valve position of the valve based on the received set point angular valve position and a difference between the measured valve conductance and a predefined metric of conductance versus angular valve position;
    determining an actual system conductance;
    determining a difference between the actual system conductance and a reference system conductance for the system; and
    generating a diagnostic indication of a fault in the system, the diagnostic indication being based on the actual angular valve position of the valve and the difference between the actual system conductance and the reference system conductance for the system; wherein,
    if the actual angular valve position is relatively high and the actual system conductance is less than the reference system conductance, in a low-conductance valve, the diagnostic indication is at least one of an at least partial blockage in a conduit of the system and degradation of a pump in the system.

14. The method of claim 13, wherein the relatively high angular valve position is greater than 50 degrees.

15. A method for providing a diagnostic indication in a vacuum system using a valve, the method comprising:

receiving a set point angular valve position based on a desired conductance of the valve;

setting actual angular valve position of the valve based on the received set point angular valve position and a difference between the measured valve conductance and a predefined metric of conductance versus angular valve position;

determining an actual system conductance;

determining a difference between the actual system conductance and a reference system conductance for the system; and generating a diagnostic indication of a fault in the system, the diagnostic indication being based on the actual angular valve position of the valve and the difference between the actual system conductance and the reference system conductance for the system; wherein, if the actual angular valve position is relatively high and the actual system conductance is less than the reference system conductance, in a non-sealing valve, the diagnostic indication is at least one of an at least partial blockage in a conduit of the system and degradation of a pump in the system.

16. The method of claim 15, wherein the relatively high angular valve position is greater than 50 degrees.

* * * * *